United States Patent
Lesieur et al.

(10) Patent No.: US 6,919,362 B2
(45) Date of Patent: Jul. 19, 2005

(54) HETEROCYCLIC DERIVATIVES, PREPARATION METHOD AND PHARMACEUTICAL COMPOSITIONS CONTAINING SAME

(75) Inventors: Daniel Lesieur, Gondecourt (FR); Elodie Blanc-Delmas, Lille (FR); Said Yous, Loos (FR); Patrick Depreux, Armentieres (FR); Gérald Guillaumet, Saint Jean le Blanc (FR); Catherine Dacquet, Paris (FR); Nigel Levens, Vaucresson (FR); Jean Albert Boutin, Suresnes (FR); Caroline Bennejean, Charenton le Pont (FR); Pierre Renard, Le Chesnay (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 10/203,113

(22) PCT Filed: Feb. 1, 2001

(86) PCT No.: PCT/FR01/00304

§ 371 (c)(1),
(2), (4) Date: Aug. 2, 2002

(87) PCT Pub. No.: WO01/57002

PCT Pub. Date: Aug. 9, 2001

(65) Prior Publication Data

US 2003/0040533 A1 Feb. 27, 2003

(30) Foreign Application Priority Data

Feb. 2, 2000 (FR) .............................. 00 01289

(51) Int. Cl.⁷ .................... A61K 31/428; A61K 31/423; C07D 263/58; C07D 277/68

(52) U.S. Cl. ...................... 514/375; 514/367; 548/169; 548/221

(58) Field of Search ................ 514/375, 367; 548/169, 221

(56) References Cited

PUBLICATIONS

Cancer and Metastasis Reviews (1998), 17(1), 91–106.*
Science (1999), vol. 286, 531–537.*

* cited by examiner

Primary Examiner—Joseph K. McKane
Assistant Examiner—Rebecca Anderson
(74) Attorney, Agent, or Firm—The Firm of Hueschen and Sage

(57) ABSTRACT

Compounds of formula (I):

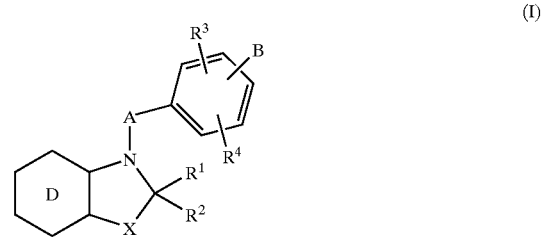

wherein:
X represents an oxygen or a sulphur or $CH_2$ or

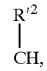
$$\underset{CH,}{\overset{R'^2}{|}}$$

$R^1$ and $R^2$ represent a hydrogen atom, or a group as defined in the description,
A represents an alkylene chain as described in the description,
B is as defined in the description,
$R^3$ and $R^4$ represent a hydrogen atom or a group as defined in the description,
D represents an optionally substituted benzene, optionally substituted pyrazine, optionally substituted pyrimidine or optionally substituted pyridazine
and medicinal products containing the same which are useful in treating or preventing melatoninergic disorders.

8 Claims, No Drawings

HETEROCYCLIC DERIVATIVES, PREPARATION METHOD AND PHARMACEUTICAL COMPOSITIONS CONTAINING SAME

This application is a 371 of PCT/FR01/00304 filed Feb. 1, 2001.

The present invention relates to new heterocyclic compounds, to a process for their preparation and to pharmaceutical compositions containing them.

The compounds described in the present invention are new and have pharmacological properties that are of special interest: they are excellent hypoglycaemic and hypolipidaemic agents.

The treatment of non-insulin dependent type II diabetes remains unsatisfactory despite the introduction onto the market of a large number of oral hypoglycaemic compounds designed to facilitate the secretion of insulin and to promote its action in peripheral target tissues.

During the last ten years, a class of compounds having a thiazolidinedione structure (U.S. Pat. Nos. 5,089,514, 5,306,726) has demonstrated a marked anti-diabetic activity by promoting sensitivity to insulin in the target peripheral tissues (skeletal muscle, liver, adipose tissue) of animal models having non-insulin dependent type II diabetes. Those compounds also lower the levels of insulin and levels of lipids in the same animal models and induce in vitro differentiation of preadipocyte cell lines into adipocyte cell lines (A. Hiragun et al., J. Cell. Physiol., 1988, 134, 124–130; R. F. Kleitzen et al., Mol. Pharmacol., 1992, 41, 393–398).

The treatment of preadipocyte cell lines with the thiazolidinedione rosiglitazone brings about induction of the expression of specific genes of the lipid metabolism, such as aP2 and adipsin, and also the expression of the glucose transporters GLUT1 and GLUT4, suggesting that the effect of the thiazolidinediones observed in vivo may be mediated via adipose tissue. That specific effect is obtained by the stimulation of nuclear transcription factors: <<peroxisome proliferator-activated receptor gamma>> (PPAR γ2). Such compounds are capable of restoring sensitivity to insulin in peripheral tissues, such as adipose tissue or skeletal muscle (J. E. Gerich, New Engl. Med., 19, 321, 1231–1245).

Compounds having a thiazolidinedione structure (troglitazone, rosiglitazone) have demonstrated disturbing side effects in man, however, including liver problems (Script N° 2470, 1999, Sep. 8th, 25).

A large number of hypoglycaemics have significant side effects (hepatic, cardiac, haematopoietic), which limit their long-term use in the treatment of non-insulin dependent type II diabetes.

The development of new therapeutic agents that are less toxic and that are active over the long term is absolutely necessary in this pathology.

Moreover, hyperlipidaemia is often observed in diabetics (Diabetes Care, 1995, 18 (supplement 1), 86/8/93). The association of hyperglycaemia and hyperlipidaemia increases the risk of cardiovascular disease in diabetics. Hyperglycaemia, hyperlipidaemia and obesity have become pathologies of the modern world marked by the intake of food in large quantities and a chronic lack of exercise.

The increase in frequency of those pathologies calls for the development of new therapeutic agents that are active in such disorders: compounds having an excellent hypoglycaemic and hypolipidaemic activity whilst avoiding the side effects observed with thiazolidinediones are consequently very beneficial in the treatment and/or prophylaxis of those pathologies, and are indicated especially in the treatment of non-insulin dependent type II diabetes for reducing peripheral insulin resistance and for normalising glucose control.

In addition to the fact that they are new, the compounds of the present invention meet the above pharmacological criteria and are excellent hypoglycaemic and hypolipidaemic agents.

The present invention relates more especially to the compounds of formula (I):

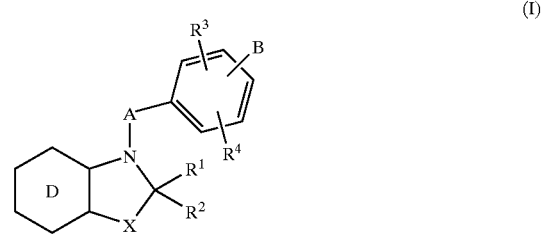

wherein:

X represents an oxygen or sulphur atom or a $CH_2$ or

group (wherein $R'^2$ together with $R^2$ forms an additional bond), $R^1$ and $R^2$, which may be identical or different, each represents a hydrogen atom, a linear or branched $(C_1-C_6)$alkyl group, an aryl group, an aryl-$(C_1-C_6)$alkyl group in which the alkyl moiety may be linear or branched, an aryloxy group, an aryl-$(C_1-C_6)$alkoxy group in which the alkoxy moiety may be linear or branched, a linear or branched $(C_1-C_6)$alkoxy group, a hydroxy group, an amino group, a linear or branched $(C_1-C_6)$alkylamino group or a dialkylamino group in which the alkyl moieties are linear or branched $C_1-C_6$, or $R^1$ and $R^2$ together form an oxo, thioxo or imino group, it being possible furthermore for $R^2$ to form with $R'^2$ an additional bond, A represents a $(C_1-C_6)$alkylene chain in which a $CH_2$ group may be replaced by a hetero atom selected from oxygen and sulphur, by an $NR_a$ group (wherein $R_a$ represents a hydrogen atom or a linear or branched $(C_1-C_6)$alkyl group), or by a phenylene or naphthylene group, B represents a linear or branched $(C_1-C_6)$alkyl group or a linear or branched $(C_2-C_6)$alkenyl group, those groups being substituted by a $R^5$ group, by a group of formula (II):

or by a group of formula (III):

$$\underset{R^6}{\overset{R^5}{\diagdown}}\!\!\!=\!\!\!\diagup\,\,\,\,\,\,\,\,\,\,\,\,\,\,(III)$$

in which groups:
the representation ═ denotes that the bond is single or double,
$R^5$ represents a $$\underset{Z}{\overset{C-Z'}{\|}}$$

group wherein Z represents a sulphur atom or an oxygen atom and Z' represents an OR or NRR' group,
and $R^6$ represents a group $$\underset{Z}{\overset{C-Z''}{\|}}$$

wherein Z" represents a Z' or R group,
(wherein R and R', which may be identical or different, each represents a R" or —C(Me)$_2$COOR" group wherein R" represents a hydrogen atom or a linear or branched ($C_1$–$C_6$)alkyl group, a linear or branched ($C_2$–$C_6$)alkenyl group, a linear or branched ($C_2$–$C_6$) alkynyl group, an aryl group, an aryl-($C_1$–$C_6$)alkyl group in which the alkyl moiety may be linear or branched, an aryl-($C_2$–$C_6$)alkenyl group in which the alkenyl moiety may be linear or branched, an aryl-($C_2$–$C_6$)alkynyl group in which the alkynyl moiety may be linear or branched, a heteroaryl group, a heteroaryl-($C_1$–$C_6$)alkyl group in which the alkyl moiety may be linear or branched, a heteroaryl-($C_2$–$C_6$)alkenyl group in which the alkenyl moiety may be linear or branched, a heteroaryl-($C_2$–$C_6$) alkynyl group in which the alkynyl moiety may be linear or branched, a ($C_3$–$C_8$)cycloalkyl group, a ($C_3$–$C_8$)cycloalkyl-($C_1$–$C_6$)alkyl group in which the alkyl moiety may be linear or branched, or a linear or branched ($C_1$–$C_6$)polyhaloalkyl group),
$R^3$ and $R^4$, which may be identical or different, each represents a hydrogen atom, a halogen atom or a R, OR or NRR' group (wherein R and R' are as defined hereinbefore),
or $R^3$ and $R^4$ together with the carbon atoms carrying them, when they are carried by two adjacent carbon atoms, form a ring that has 5 or 6 ring members and that may contain a hetero atom selected from oxygen, sulphur and nitrogen,
D represents:
a benzene nucleus, in which case X cannot represent a group $$\underset{CH}{\overset{R'^2}{|}}$$

as defined hereinbefore,
or D represents a pyridine, pyrazine, pyrimidine or pyridazine nucleus, those nuclei being unsubstituted or substituted by from 1 to 3 identical or different groups selected from R, OR, S(O)$_n$R, $$C(Z)R,\,\,\,\,\,\underset{}{\overset{OR}{\underset{|}{CH}}}\!\!-R',$$

C(Z)OR, NRR', C(Z)NRR', $$\underset{}{\overset{R}{\underset{|}{C}}}\!\!=\!\!N\!\!-\!\!OR',\,\,\,\,\,\underset{}{\overset{R}{\underset{|}{N}}}\!\!-\!\!C(Z)R',\,\,\,\,\,\underset{}{\overset{R}{\underset{|}{N}}}\!\!-\!\!C(Z)OR'$$

(in which groups R, R' and Z are as defined hereinbefore and n is 0, 1 or 2), cyano, nitro and halogen atoms,
wherein:
when A represents a CH$_2$ group, B cannot represent a linear or branched ($C_1$–$C_6$)alkyl group substituted by a group $$\underset{Z}{\overset{C-NRR'}{\|}},$$

when the groups A and B are in the ortho position in relation to one another on the benzene nucleus carrying them, B cannot represent a linear or branched ($C_2$–$C_6$)-alkenylene group substituted by a group $$\underset{O}{\overset{C-Z'}{\|}},$$

when A represents a group

—CH$_2$—⟨phenyl⟩—,

B cannot represent a —CH$_2$—COOH group,
aryl is to be understood as a phenyl, naphthyl or biphenyl group, which groups may be partially hydrogenated,
heteroaryl is to be understood as any mono- or bi-cyclic aromatic group containing from 5 to 10 ring members, which may be partially hydrogenated on one of the rings in the case of bicyclic heteroaryls, and which contains from 1 to 3 hetero atoms selected from oxygen, nitrogen and sulphur,
wherein the aryl and heteroaryl groups so defined may be substituted by from 1 to 3 groups selected from linear or branched ($C_1$–$C_6$)alkyl, linear or branched ($C_1$–$C_6$)alkoxy, carboxy, formyl, NR$_b$R$_c$ (wherein R$_b$ and R$_c$, which may be identical or different, each represents a hydrogen atom, a linear or branched ($C_1$–$C_6$)alkyl group, an,aryl group or a heteroaryl group), ester, amido, nitro, cyano, O—C(Me)$_2$COOR" (wherein R" is as defined hereinbefore) and halogen atoms,
to their enantiomers and diastereoisomers, and also to pharmaceutically acceptable addition salts thereof with an acid or a base.
Amongst the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric, oxalic acid, etc . . .

Amongst the pharmaceutically acceptable bases there may be mentioned, without implying any limitation, sodium hydroxide, potassium hydroxide, triethylamine, tert-butylamine, etc . . .

Preferred compounds of the invention are the compounds of formula (I) wherein $R^1$ and $R^2$ together form an oxo group.

A preferred group for $R^3$ and $R^4$ is the hydrogen atom.

Preferably, A represents an alkylene chain in which a $CH_2$ group may be replaced by a hetero atom.

The invention relates more especially to compounds of formula (I) wherein A represents an ethyleneoxy group.

Preferred groups D are the benzene nucleus, and the pyridine nucleus.

Preferred groups D are the benzene nucleus and the pyridine nucleus, those groups being unsubstituted or substituted, preferably in the 6 position, and more especially by a group C(Z)R (such as the groups benzoyl, halobenzoyl, biphenylcarbonyl, naphthoyl, alkoyl, pyridylcarbonyl, alkoxybenzoyl, alkylbenzoyl), R (such as, for example, the groups benzyl, halobenzyl, alkylbenzyl, alkoxybenzyl, biphenylmethyl, phenylyinyl),

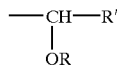

(such as, for example, (hydroxy)(phenyl)methyl),

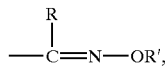

(such as, for example, (alkoxyimino)(phenyl)methyl, (hydroxyimino)(phenyl)methyl, (alkoxyimino)(halophenyl) methyl), C(Z)NRR', (such as, for example, the group CONHPh), or

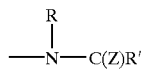

(such as, for example, the group NHCOPh).

X preferably represents an oxygen atom or a sulphur atom or, when D represents a pyridine nucleus, a group $CHR'^2$.

Preferred groups B are as follows:

alkyl or alkenyl groups substituted by a group of formula (II) and, more especially, alkyl groups substituted by a group of formula (II), such as, for example, the group

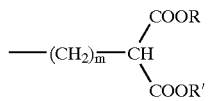

wheren m is 1 or 2, and R and R', which may be identical or different, each represents a hydrogen atom or an alkyl group, such as methyl or ethyl for example, the group

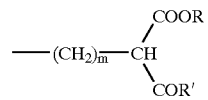

wherein m is 1 or 2,
R preferably represents a hydrogen atom or an alkyl group, such as methyl or ethyl for example, and R' advantageously represents an aryl group, such as, for example, optionally substituted phenyl,
or the group

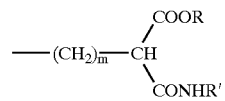

wherein m is 1 or 2 and R and R', which may be identical or different, each represents a hydrogen atom or an alkyl group, such as methyl or ethyl for example, alkyl or alkenyl groups substituted by a $R^5$ group, and more especially alkyl groups substituted by a $R^5$ group, such as, for example, the group $—(CH_2)_p—COOR$ wherein p is 1, 2 or 3 and R represents a hydrogen atom or an alkyl group, such as methyl or ethyl for example, or aryl, such as phenyl for example.

Even more especially, the invention relates to the following compounds of formula (I):
diethyl 2-{4-[2-(2-oxo-1,3-benzoxazol-3(2H)-yl)ethoxy] benzylidene}malonate,
diethyl 2-{4-[2-(2-oxo-1,3-benzoxazol-3(2H)-yl)ethoxy] benzyl}malonate,
3-ethoxy-3-oxo-2-{4-[2-(2-oxo-1,3-benzoxazol-3(2H)-yl) ethoxy]benzyl}propanoic acid,
2-{4-[2-(2-oxo-1,3-benzoxazol-3(2H)-yl)ethoxy] benzyl}malonic acid,
diethyl 2-{4-[2-(2-oxo-1,3-benzothiazol-3(2H)-yl)ethoxy] benzylidene}malonate,
dimethyl 2-{4-[2-(2-oxo-1,3-benzothiazol-3(2H)-yl)ethoxy] benzylidene}malonate,
diethyl 2-{4-[2-(2-oxo-1,3-benzothiazol-3(2H)-yl)ethoxy] benzyl}malonate,
dimethyl 2-{4-[2-(2-oxo-1,3-benzothiazol-3(2H)-yl)ethoxy] benzyl}malonate,
3-methoxy-3-oxo-2-{4-[2-(2-oxo-1,3-benzothiazol-3(2H)-yl)ethoxy]benzyl}propanoic acid,
3-ethoxy-3-oxo-2-{4-[2-(2-oxo-1,3-benzothiazol-3 (2H)-yl) ethoxy]benzyl}propanoic acid,
2-{4-[2-(2-oxo-1,3-benzothiazol-3(2H)-yl)ethoxy] benzyl}malonic acid,
diethyl 2-{4-[3-(2-oxo-1,3-benzothiazol-3(2H)-yl)propoxy] benzylidene}malonate,
tert-butyl methyl 2-{4-[2-(2-oxo-1,3-benzothiazol-3(2H)-yl)ethoxy]benzylidene}propanedioate,
tert-butyl methyl 2-{4-[2-(2-oxo-1,3-benzothiazol-3(2H)-yl)ethoxy]benzyl}malonate,
dimethyl 2-{4-[2-(6-benzoyl-2-oxo-1,3-benzothiazol-3 (2H)-yl)ethoxy]benzylidene}malonate,
dimethyl 2-{4-[2-(6-benzoyl-2-oxo-1,3-benzothiazol-3 (2H)-yl)ethoxy]benzyl}malonate,
dimethyl 2-{4-[2-(6-benzyl-2-oxo-1,3-benzothiazol-3(2H)-yl)ethoxy]benzyl}malonate,
dimethyl 2-{4-[2-(6-benzoyl-2-oxo-1,3-benzoxazol-3(2H)-yl)ethoxy]benzylidene}malonate, dimethyl 2-{4-[2-(6-benzoyl-2-oxo-1,3-benzoxazol-3(2H)-yl)ethoxy]benzyl}malonate,
dimethyl 2-{4-[2-(6-benzyl-2-oxo-1,3-benzoxazol-3(2H)-yl)ethoxy]benzyl}malonate,
3-{4-[2-(2-oxo-1,3-benzoxazol-3(2H)-yl)ethoxy]phenyl}-2-propenoic acid,
3-{4-[2-(2-oxo-1,3-benzoxazol-3(2H)-yl)ethoxy]phenyl}-2-propanoic acid,
3-{4-[2-(2-oxo-1,3-benzothiazol-3(2H)-yl)ethoxy]phenyl}-2-propenoic acid,
3-{4-[2-(2-oxo-1,3-benzothiazol-3(2H)-yl)ethoxy]phenyl}-2-propanoic acid,
dimethyl 2-{4-[2-(2-oxo[1,3]oxazolo[4,5-b]pyrid-3(2H)-yl)ethoxy]benzyl}malonate,
dimethyl 2-{4-[2-(1H-pyrrolo[2,3-b]pyrid-1-yl)ethoxy]benzyl}malonate,
methyl 3-{4-[2-(6-benzoyl-2-oxo-1,3-benzothiazol-3(2H)-yl)ethoxy]phenyl}propanoate,
dimethyl 2-{4-[2-(6-[hydroxy(phenyl)methyl]-2-oxo-1,3-benzoxazol-3(2H)-yl)ethoxy]benzyl}malonate,
methyl 3-{4-[2-(6-benzoyl-2-oxo-1,3-benzoxazol-3(2H)-yl)ethoxy]phenyl}propanoate,
dimethyl 2-{4-[2-(6-[hydroxy(phenyl)methyl]-2-oxo-1,3-benzothiazol-3(2H)-yl)ethoxy]benzyl}malonate,
dimethyl 2-{4-[2-(6-[(methoxyimino)(phenyl)methyl]-2-oxo-1,3-benzothiazol-3(2H)-yl)ethoxy]benzyl}malonate,
dimethyl 2-{4-[2-(6-(2-chlorobenzoyl)-2-oxo-1,3-benzothiazol-3(2H)-yl)ethoxy]benzyl}malonate,
dimethyl 2-{4-[2-(6-[(hydroxyimino)(phenyl)methyl]-2-oxo-1,3-benzothiazol-3(2H)-yl)ethoxy]benzyl}malonate,
dimethyl 2-{4-[2-(6-([1,1'-biphenyl]-4-ylcarbonyl)-2-oxo-1,3-benzothiazol-3(2H)-yl)ethoxy]benzyl}malonate,
dimethyl 2-{4-[2-(6-([1,1'-biphenyl]-4-ylmethyl)-2-oxo-1,3-benzothiazol-3(2H)-yl)ethoxy]benzyl}malonate,
dimethyl 2-{4-[2-(6-(1-naphthoyl)-2-oxo-1,3-benzothiazol-3(2H)-yl)ethoxy]benzyl}malonate,
dimethyl 2-{4-[2-(6-(3-chlorobenzoyl)-2-oxo-1,3-benzothiazol-3(2H)-yl)ethoxy]benzyl}malonate,
dimethyl 2-{4-[2-(6-(2-chlorobenzyl)-2-oxo-1,3-benzothiazol-3(2H)-yl)ethoxy]benzyl}malonate,
dimethyl 2-{4-[2-(6-(3-chlorobenzyl)-2-oxo-1,3-benzothiazol-3(2H)-yl)ethoxy]benzyl}malonate,
dimethyl 2-{4-[2-(6-(1-naphthylmethyl)-2-oxo-1,3-benzothiazol-3(2H)-yl)ethoxy]benzyl}malonate,
dimethyl 2-{4-[2-(2-oxo-6-(3-pyridylcarbonyl)-1,3-benzothiazol-3(2H)-yl)ethoxy]benzyl}malonate,
dimethyl 2-{4-[2-(6-(4-chlorobenzoyl)-2-oxo-1,3-benzothiazol-3(2H)-yl)ethoxy]benzyl}malonate,
2-{4-[2-(6-benzoyl-2-oxo-1,3-benzothiazol-3(2H)-yl)ethoxy]benzyl}malonic acid
dimethyl 2-{4-[2-(6-(2-naphthoyl)-2-oxo-1,3-benzothiazol-3(2H)-yl)ethoxy]benzyl}malonate,
dimethyl 2-{4-[2-(6-(4-methoxybenzoyl)-2-oxo-1,3-benzothiazol-3(2H)-yl)ethoxy]benzyl}malonate
dimethyl 2-{4-[2-(6-(4-chlorobenzyl)-2-oxo-1,3-benzothiazol-3(2H)-yl) ethoxy]benzyl}malonate,
2-{4-[2-(6-benzoyl-2-oxo-1,3-benzothiazol-3(2H)-yl)ethoxy]benzyl}-3-methoxy-3-oxopropanoic acid,
dimethyl 2-{4-[2-(6-[(3-chlorophenyl)(methoxyimino)methyl]-2-oxo-1,3-benzothiazol-3(2H)-yl)ethoxy]benzyl}malonate,
dimethyl 2-{4-[2-(6-[[1,1'-biphenyl]-4-yl(methoxyimino)methyl]-2-oxo-1,3-benzothiazol-3(2H)-yl)ethoxy]benzyl}malonate,
3-methoxy-3-oxo-2-{4-[2-(1H-pyrrolo[2,3-b]pyrid-1-yl)ethoxy]benzyl}propanoic acid,
dimethyl 2-{4-[2-(6-(benzoylamino)-2-oxo-1,3-benzothiazol-3(2H)-yl)ethoxy]benzyl}malonate,
methyl 3-{4-[2-(6-benzyl-2-oxo-1,3-benzothiazol-3(2H)-yl)ethoxy]phenyl}propanoate,
methyl 3-{4-[2-(6-[(methoxyimino)(phenyl)methyl]-2-oxo-1,3-benzothiazol-3(2H)-yl)ethoxy]phenyl}propanoate,
3-{4-[2-(6-benzoyl-2-oxo-1,3-benzothiazol-3(2H)-yl)ethoxy]phenyl}propanoic acid,
2-{4-[2-(1H-pyrrolo[2,3-b]pyrid-1-yl)ethoxy]benzyl}malonic acid,
methyl 2-{4-[2-(6-benzoyl-2-oxo-1,3-benzothiazol-3(2H)-yl)ethoxy]benzyl}-3-(methylamino)-3-oxopropanoate,
dimethyl 2-{4-[2-(6-(anilinocarbonyl)-2-oxo-1,3-benzothiazol-3(2H)-yl)ethoxy]benzyl}malonate,
dimethyl 2-(4-{[2-(6-benzoyl-2-oxo-1,3-benzothiazol-3(2H)-yl)ethyl]amino}benzyl)malonate,
dimethyl 2-{4-[2-(2-oxo-6-[2-phenylethenyl]-1,3-benzothiazol-3(2H)-yl)ethoxy]benzyl}malonate.

The enantiomers, diastereoisomers, and also pharmaceutically acceptable addition salts with an acid or a base of the preferred compounds of the invention form an integral part of the invention.

The present invention relates also to a process for the preparation of compounds of formula (I) which is characterised in that there is used as starting material a compound of formula (IV):

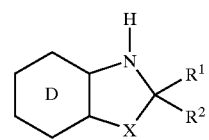

(IV)

wherein $R^1$, $R^2$, X and D are as defined for formula (I), which is condensed in basic medium with a compound of formula (V):

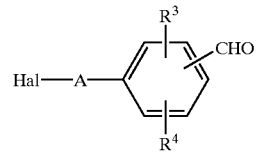

(V)

wherein Hal represents a halogen atom and A, $R^3$ and $R^4$ are as defined for formula (I), to yield a compound of formula (VI):

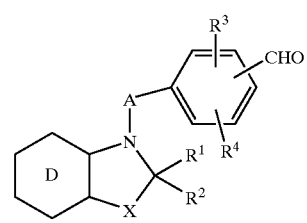

(VI)

wherein A, D, X, $R^1$, $R^2$, $R^3$ and $R^4$ are as defined hereinbefore, which is condensed in basic medium with a compound of formula (VII):

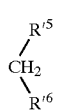
(VII)

wherein R'^5 and R'^6 may have any of the meanings given hereinbefore for R^5 and R^6 with the exception of the group COOH,
to obtain a compound of formula (I/a), a particular case of the compounds of formula (I):

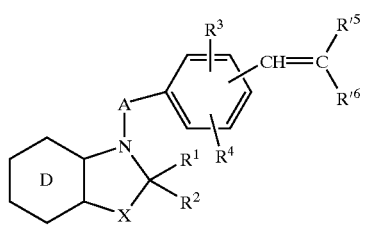
(I/a)

wherein D, A, X, R^2, R^3, R^3, R^4, R'^5 and R'^6 are as defined hereinbefore,
which is hydrogenated in the presence of a catalyst, such as palladium-on-carbon for example, to yield a compound of formula (I/b), a particular case of the compounds of formula (I):

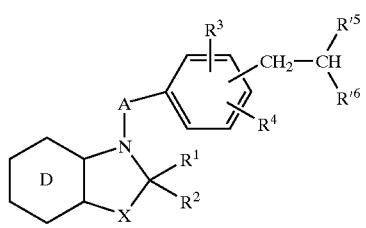
(I/b)

wherein D, A, X, R^1, R^2, R^3, R^4, R'^5 and R'^6 are as defined hereinbefore,
(it being possible for the compounds of formulae (I/a) and (I/b) to be obtained by direct condensation of a compound of formula (IV) with a compound of formula (V')):

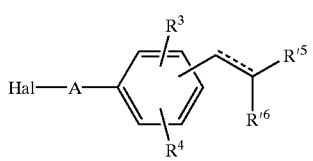
(V')

wherein Hal represents a halogen atom and A, R^3, R^4, R'^5 and R'^6 are as defined hereinbefore),
or which compound of formula (VI) is condensed, under the conditions of a Horner-Emmons reaction, with a corresponding phosphonic compound of a compound of formula (VIII):

Hal-CH_2-B'  (VIII)

wherein Hal represents a halogen atom and B' represents a linear or branched $(C_1–C_5)$alkyl group or linear or branched $(C_2–C_5)$alkenyl group, those groups being substituted by a R'^5 group, by a group of formula (II')

(II')

or by a group of formula (III')

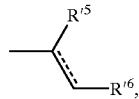
(III')

in which groups R'^5 and R'^6 and the representation ══ are as defined hereinbefore,
to yield a compound of formula (I/c), a particular case of the compounds of formula (I):

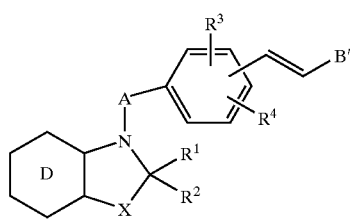
(I/c)

wherein D, X, A, B', R^1, R^2, R^3 and R^4 are as defined hereinbefore,
which may be subjected to catalytic hydrogenation, in the presence of palladium for example, to obtain a compound of formula (I/d), a particular case of the compounds of formula (I):

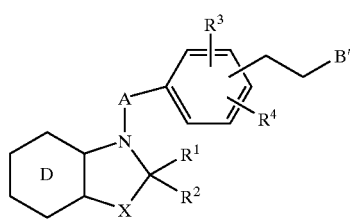
(I/d)

wherein D, A, X, B', R^1, R^2, R^3 and R^4 are as defined hereinbefore,
or which compound of formula (VI) is converted into a corresponding acid chloride which is condensed, in the presence of a palladium or tin compound for example, with a compound of formula (IX):

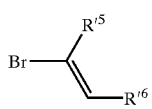
(IX)

wherein R'⁵ and R'⁶ are as defined hereinbefore,
to yield a compound of formula (X)

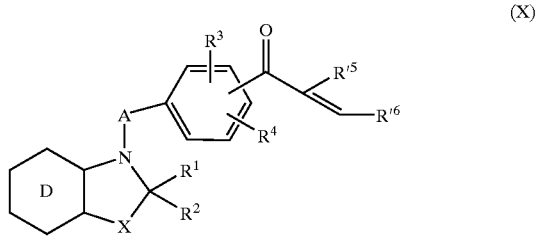

wherein D, X, A, R¹, R², R³, R⁴, R'⁵ and R'⁶ are as defined hereinbefore,
which is subjected to the action of a reducing agent, such as Et₃SiH for example, to yield a compound of formula (I/e), a particular case of the compounds of formula (I):

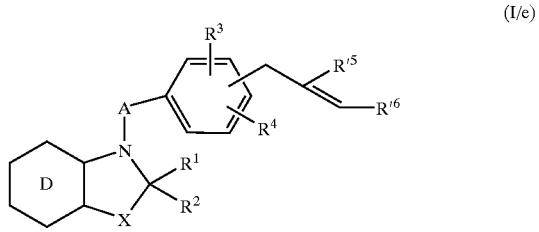

wherein D, X, A, R¹, R², R³, R⁴, R'⁵ and R'⁶ are as defined hereinbefore,
wherein the compounds of formula (I/a), (I/b), (I/c), (I/d) or (I/e) in which R'⁵ and R'⁶ represent ester groups may be fully or partially hydrolysed to yield corresponding gem-dicarboxylated or hemicarboxylated compounds of formula (I/f), a particular case of the compounds of formula (I):

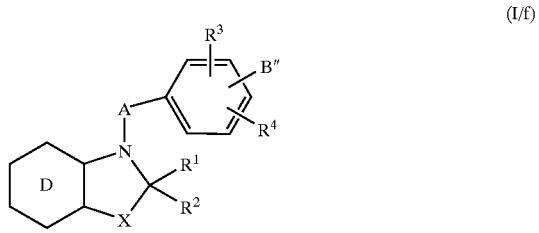

wherein D, X, A, R¹, R², R³ and R⁴ are as defined hereinbefore and B" represents a group as defined hereinbefore for B in which R⁵ and/or R⁶ represent(s) a group COOH,
(it being possible for the compounds of formula (I/f) wherein B" represents a group —CH=CH—COOH to be obtained directly from a compound of formula (VI) by the condensation of malonic acid under decarboxylating conditions and for them to be reduced to yield compounds of formula (I/f) wherein B" represents a group —CH₂—CH₂—COOH),
the compounds of formulae (I/a) to (I/f) constituting the totality of the compounds of the invention, which compounds may be purified according to a conventional separation technique, are converted, if desired, into addition salts with a pharmaceutically acceptable acid or base, and are optionally separated into their isomers according to a conventional separation technique.

The compounds of formulae (IV) and (V) are commercially available or can readily be obtained by the person skilled in the art by conventional chemical reactions or chemical reactions described in the literature.

The compounds of the present invention have very valuable pharmacological properties.

The compounds demonstrate especially an excellent activity in lowering blood glucose levels. As a result of such properties they can be used therapeutically in the treatment and/or prophylaxis of hyperglycaemia, dyslipidaemia and, more especially, in the treatment of non-insulin dependent type II diabetes, glucose intolerance, disorders associated with syndrome X (including hypertension, obesity, insulin resistance, atherosclerosis, hyperlipidaemia), coronary artery disease and other cardiovascular diseases (including arterial hypertension, cardiac insufficiency, venous insufficiency), renal disorders (including glomerulonephritis, glomerulosclerosis, nephrotic syndrome, hypertensive nephrosclerosis), retinopathy, disorders associated with the activation of endothelial cells, psoriasis, polycystic ovary syndrome, dementia, diabetic complications and osteoporosis.

They can be used as aldose reductase inhibitors for improving cognitive functions in dementia and the complications of diabetes, intestinal inflammatory disorders, myotonic dystrophy, pancreatitis, arteriosclerosis, xanthoma.

The activity of these compounds is also recommended for the treatment and/or prophylaxis of other diseases, including type I diabetes, hypertriglyceridaemia, syndrome X, insulin resistance, dyslipidaemia in diabetics, hyperlipidaemia, hypercholesterolaemia, arterial hypertension, cardiac insufficiency, and cardiovascular disease, especially atherosclerosis.

The compounds are furthermore indicated for use in the regulation of appetite, especially in the regulation of food intake in subjects suffering from disorders such as obesity, anorexia, bulimia and anorexia nervosa.

The compounds can accordingly be used in the prevention or treatment of hypercholesterolaemia, obesity with advantageous effects on hyperlipidaemia, hyperglycaemia, osteoporosis, glucose intolerance, insulin resistance or disorders in which insulin resistance is a secondary physio-pathological mechanism.

The use of those compounds enables reduction of total cholesterol, body weight, leptin resistance, plasma glucose, triglycerides, LDLs, VLDLs and also plasma free fatty acids. The compounds can be used in association with HMG CoA reductase inhibitors, fibrates, nicotinic acid, cholestyramine, colestipol or probucol, and can be administered together or at different times to act in synergy in the patient treated.

They furthermore exhibit activity in cancer pathologies and especially hormone-dependent cancers, such as breast cancer or colon cancer, and also have an inhibiting effect on the angiogenesis processes implicated in such pathologies.

Amongst the pharmaceutical compositions according to the invention there may mentioned more especially those which are suitable for oral, parenteral, nasal, per- or transcutaneous, rectal, perlingual, ocular or respiratory administration and especially tablets or dragées, sublingual tablets, sachets, paquets, gelatin capsules, glossettes, lozenges, suppositories, creams, ointments, dermal gels and drinkable or injectable ampoules.

The dosage varies in accordance with the sex, age and weight of the patient, the administration route, the nature of the therapeutic indication, or any associated treatments, and ranges from 0.1 mg to 1 g per 24 hours taken in 1 or more administrations.

The Examples which follow illustrate the invention and do not limit it in any way. The following Preparations result in synthesis intermediates for use in the preparation of the invention.

Preparation 1: 4-[2-(2-Oxo-1,3-benzoxazol-3(2H)-yl)ethoxy]benzaldehyde

Step A: 4-(2-Chloroethoxy)benzaldehyde

Dissolve 4-hydroxybenzaldehyde (0.082 mol) in dimethylformamide (100 ml) and add potassium carbonate (0.164 mol) and 1-bromo-2-chloroethane (0.246 mol). Stir magnetically for five days at ambient temperature, then hydrolyse the reaction mixture in 500 ml of water and render alkaline with 3 g of sodium hydroxide pellets. Extract twice with 50 ml of ether each time. Dry the organic phase over magnesium sulphate and remove the ether by evaporation under reduced pressure. Purify the resulting oil by flash chromatography using a 9/1 cyclohexane/ether mixture as eluant. Subsequently, remove the mixture of solvents by evaporation under reduced pressure and crystallise the resulting yellow oil and store it in a dessicator.

Melting point: 38–40° C.

Step B: 4-[2-(2-Oxo-1,3-benzoxazol-3(2H)-yl)ethoxy]benzaldehyde

Dissolve benzoxazolinone (0.024 mol) in dimethylformamide and add potassium carbonate (0.047 mol). Heat at reflux for 20 minutes and then add the compound obtained in Step A (0.021 mol). Stir magnetically at reflux for 80 minutes. Hydrolyse the reaction mixture in 150 ml of water, suction-filter off the resulting precipitate and recrystallise it from a 5/5 cyclohexane/toluene mixture.

Melting point: 112–113° C.

Preparation 2: 4-[2-(2-Oxo-1,3-benzothiazol-3(2H)-yl)ethoxy]benzaldehyde

The procedure is as in Preparation 1, with the replacement of benzoxazolinone with benzothiazolinone.

Melting point: 118–120° C.

Preparation 3: 4-[3-(2-Oxo-1,3-benzothiazol-3(2H)-yl)propoxy]benzaldehyde

The procedure is as in Preparation 1, with the replacement of 1-bromo-2-chloroethane with 1-bromo-3-chloropropane in Step A and of benzoxazolinone with benzothiazolinone in Step B.

Preparation 4: 4-[2-(6-Benzoyl-2-oxo-1,3-benzothiazol-3(2H)-yl)ethoxyl]benzaldehyde Step A: 6-Benzoylbenzothiazolinone Grind benzothiazolinone (10 g) and benzoic acid (9.7 g) in a mortar. Introduce the preparation into a flask and add polyphosphoric acid (100 g). Heat at 140° C. for 4 hours with mechanical stirring. Hydrolyse the reaction mixture in ice. Remove the resulting precipitate by filtration, wash it with ether and recrystallise from a 4/6 cyclohexane/toluene mixture.

Melting point: 190° C.

Step B: 4-[2-(6-Benzoyl-2-oxo-1,3-benzothiazol-3(2H)-yl)ethoxy]benzaldehyde

The procedure is as in Step B of Preparation 1, with the replacement of benzoxazolinone with the compound obtained in Step A.

Melting point: 135–139° C.

Preparation 5: 4-[2-(6-Benzoyl-2-oxo-1,3-benzoxazol-3(2H)-yl)ethoxy]benzaldehyde The procedure is as in Preparation 4, starting from benzoxazolinone.

Melting point: 105–108° C.

Preparation 6: 4-[2-(2-Oxo[1,3]oxazolo[4,5-b]pyrid-3(2H)-yl)ethoxy]benzaldehyde The procedure is as in Preparation 1, with the replacement of benzoxazolinone with [1,3]oxazolo[4,5-b]pyrid-2(3H)-one.

Preparation 7: 4-[2-(1H-Pyrrolo[2,3-b]pyrid-1-yl)ethoxy]benzaldehyde

The procedure is as in Preparation 1, with the replacement of benzoxazolinone with 1H-pyrrolo[2,3-b]pyridine.

Preparation 8: 4-[2-(1H-Pyrrolo[3,2-c]pyrid-1-yl)ethoxy]benzaldehyde

The procedure is as in Preparation 1, with the replacement of benzoxazolinone with 1H-pyrrolo[3,2-c]pyridine.

EXAMPLE 1

Diethyl 2-{4-[2-(2-oxo-1,3-benzoxazol-3(2H)-yl)ethoxy]benzylidene}malonate

Dissolve the compound obtained Preparation 1 (1.20 g) in toluene (80 ml) and then add piperidine (0.02 ml), glacial acetic acid (0.05 ml) and diethyl malonate (0.70 ml). Heat at the boil for 5 days with the removal of water by azeotropic distillation using a Dean-Stark apparatus. Allow to cool and then remove the toluene by evaporation under reduced pressure. Carry out flash chromatography using dichloromethane as eluant in order to purify the resulting oil. Remove the dichloromethane by evaporation under reduced pressure. Crystallise the oil from ether, remove the resulting solid by filtration and recrystallise it from a 5/5 cyclohexane/toluene mixture.

Melting point: 98–100° C.

EXAMPLE 2

Diethyl 2-{4-[2-(2-oxo-1,3-benzoxazol-3(2H)-yl)ethoxy]benzyl}malonate

Dissolve the compound obtained in Example 1 (6.7 g) in a dioxane/absolute ethanol mixture (100 ml/20 ml) and add palladium-on-carbon (0.5 g). Stir magnetically at ambient temperature under a hydrogen atmosphere for 76 hours. Remove the palladium-on-carbon by filtration and remove the mixture of solvents by evaporation under reduced pressure. Crystallise the resulting oil by trituration in isopropyl ether. Recrystallise the resulting precipitate from a 9/1 cyclohexane/toluene mixture.

Melting point: 68–70° C.

EXAMPLE 3

3-Ethoxy-3-oxo-2-{4-[2-(2-oxo-1,3-benzoxazol-3(2H)-yl)ethoxy]benzyl}propanoic acid Dissolve the compound obtained in Example 2 (0.5 g) in absolute ethanol (6.5 ml) and add tetrahydrofuran (2 ml). Subsequently, cool the reaction mixture using an ice bath and add 2N sodium hydroxide (0.7 ml). Stir magnetically for 18 hours at ambient temperature. Remove the absolute ethanol/tetrahydrofuran mixture by evaporation under reduced pressure. Take up the resulting residue in water and extract twice with 50 ml of ether each time. Acidify the aqueous phase with a 6N hydrochloric acid solution until a pH of 1 is obtained, then extract twice with 50 ml of ether each time. Dry the organic phase over magnesium sulphate and remove the ether by evaporation under reduced pressure.

Oil.

EXAMPLE 4

2-{4-[2-(2-oxo-1,3-benzoxazol-3(2H)-yl)ethoxy]benzyl}malonic acid

Dissolve the compound obtained in Example 2 (1.5 g) in tetrahydrofuran (20 ml). Add 2N sodium hydroxide (8 ml) to the reaction mixture, cooled to 0° C. using an ice bath. Stir magnetically at ambient temperature for 72 hours. Remove the tetrahydrofuran by evaporation under reduced pressure. Take up the resulting residue in a 6N hydrochloric acid solution to pH 1 and extract twice with 50 ml of ether each time. Dry the organic phase over magnesium sulphate and remove the ether by evaporation under reduced pressure. Crystallise the resulting oil from isopropyl ether and recrystallise the resulting precipitate from cyclohexane.

Melting point: 118–120° C.

EXAMPLE 5

Diethyl 2-{4-[2-(2-oxo-1,3-benzothiazol-3(2H)-yl)ethoxy]benzylidene}malonate

The procedure is as in Example 1, starting from the compound obtained in Preparation 2.

Melting point: 113–114° C.

EXAMPLE 6

Dimethyl 2-{4-[2-(2-oxo-1,3-benzothiazol-3(2H)-yl)ethoxy]benzylidene}malonate

The procedure is as in Example 1, starting from the compound obtained in Preparation 2 and with the replacement of diethyl malonate with dimethyl malonate.

Melting point: 144–146° C.

EXAMPLE 7

Diethyl 2-{4-[2-(2-oxo-1,3-benzothiazol-3(2H)-yl)ethoxy]benzyl}malonate

The procedure is as in Example 2, starting from the compound obtained in Example 5.

Oil.

EXAMPLE 8

Dimethyl 2-{4-[2-(2-oxo-1,3-benzothiazol-3(2H)-yl)ethoxy]benzyl}malonate

Dissolve the compound obtained in Example 6 (3 g) in a methanol/dioxane mixture (50 ml/50 ml) and add palladium-on-carbon (0.75 g). Leave at ambient temperature under a hydrogen atmosphere for 5 hours with magnetic stirring. Remove the palladium-on-carbon by filtration and remove the methanol/dioxane mixture by evaporation under reduced pressure. Crystallise the resulting oil from isopropyl ether.

Melting point: 67–70° C.

EXAMPLE 9

3-Methoxy-3-oxo-2-{4-[2-(2-oxo-1,3-benzothiazol-3(2H)-yl)ethoxy]benzyl}propanoic acid Dissolve the compound obtained in Example 8 (0.5 g) in methanol (30 ml) and add potassium hydroxide (0.07 g) that has previously been dissolved in methanol. Leave for one week at ambient temperature with magnetic stirring. Remove the methanol by evaporation under reduced pressure and acidify the resulting residue with a 6N hydrochloric acid solution until a pH of 1 is obtained. Extract twice with 30 ml of ether each time and then evaporate the organic phase under reduced pressure after having dried it over magnesium sulphate. Precipitate the resulting residue in ether and filter off the precipitate which forms.

Melting point: 30–35° C.

EXAMPLE 10

3-Ethoxy-3-oxo-2-{4-[2-(2-oxo-1,3-benzothiazol-3(2H)-yl)ethoxy]benzyl}propanoic acid Dissolve the compound obtained in Example 7 (0.85 g) in absolute ethanol (20 ml) and cool the reaction mixture using an ice bath. Add potassium hydroxide (0.10 g) and stir magnetically for 90 hours at ambient temperature. Remove the absolute ethanol by evaporation under reduced pressure. Take up the residue in 20 ml of water and extract twice with 30 ml of ether each time. Acidify the aqueous phase with a hydrochloric acid solution until a pH of 1 is obtained. Extract twice with 30 ml of ether each time. Dry the organic phase over magnesium sulphate and remove the ether by evaporation under reduced pressure.

Oil.

EXAMPLE 11

2-{4-[2-(2-Oxo-1,3-benzothiazol-3(2H)-yl)ethoxy]benzyl}malonic acid

Dissolve the compound obtained in Example 7 (1 g) in an absolute ethanol/tetrahydrofuran mixture (13 ml/2 ml). Add 2N sodium hydroxide (2.5 ml) to the reaction mixture which has been cooled to 0° C. using an ice bath. Stir magnetically at ambient temperature for 48 hours. Remove the absolute ethanol/tetrahydrofuran mixture by evaporation under reduced pressure. Take up the resulting residue with a hydrochloric acid solution to pH 1 and extract twice with 50 ml of ethyl acetate each time. Dry the organic phase over magnesium sulphate and remove the ethyl acetate by evaporation under reduced pressure. Suction-filter and wash the resulting precipitate with ether and then recrystallise it from acetonitrile.

Melting point: 179–181° C.

EXAMPLE 12

Diethyl 2-{4-[3-(2-oxo-1,3-benzothiazol-3(2H)-yl)propoxy]benzylidene}malonate

The procedure is as in Example 1, starting from the compound obtained in Preparation 3.

EXAMPLE 13

Diethyl 2-{4-[3-(2-oxo-1,3-benzothiazol-3(2H)-yl)propoxy]benzyl}malonate

The procedure is as in Example 2, starting from the compound obtained in Example 12.

EXAMPLE 14

2-{4-[3-(2-Oxo-1,3-benzothiazol-3(2H)-yl)propoxy]benzyl}malonic acid

The procedure is as in Example 4, starting from the compound obtained in Example 13.

EXAMPLE 15 tert-Butyl methyl 2-{4-[2-(2-oxo-1,3-benzothiazol-3(2H)-yl)ethoxy]benzylidene}propanedioate The procedure is as in Example 1, starting from the compound obtained in Preparation 2 and with the replacement of diethyl malonate with tert-butyl methyl malonate.

EXAMPLE 16 tert-Butyl-methyl 2-{4-[2-(2-oxo-1,3-benzothiazol-3 (2H)-yl)ethoxy]benzyl}malonate The procedure is as in Example 2, starting from the compound obtained in Example 15.

Oil.

EXAMPLE 17

Dimethyl 2-{4-[2-(6-benzoyl-2-oxo-1,3-benzothiazol-3(2H)-yl)-ethoxy]benzylidene}malonate The procedure is as in Example 1, starting from the compound obtained in Preparation 4 and with the replacement of diethyl malonate with dimethyl malonate.

Melting point: 167–170° C.

EXAMPLE 18

Dimethyl 2-{4-[2-(6-benzoyl-2-oxo-1,3-benzothiazol-3(2H)-yl)-ethoxy]benzyl}malonate Dissolve the compound obtained in Example 17 (3.7 g) in a methanol/tetrahydrofuran/dioxane mixture (10 ml/30 ml/30 ml) and add palladium-on-carbon (0.9 g). Stir magnetically under a hydrogen atmosphere at ambient temperature for 24 hours. Remove the palladium-on-carbon by filtration and remove the mixture of solvents by evaporation under reduced pressure. The product obtained is recrystallised from isopropyl ether.

Melting point: 65–67° C.

EXAMPLE 19

Dimethyl 2-{4-[2-(6-benzyl-2-oxo-1,3-benzothiazol-3(2H)-yl)-ethoxy]benzyl}malonate Dissolve the compound obtained in Example 18 (0.7 g) in trifluoroacetic acid (1.6 ml) and then add triethylsilane (0.5 ml). Leave at ambient temperature for 2 days with magnetic stirring. Hydrolyse the reaction mixture and then extract twice with 30 ml of ether each time. Dry the organic phase over magnesium sulphate and evaporate it under reduced pressure. Carry out flash chromatography on the resulting residue using an 8/2 cyclohexane/ethyl acetate mixture as eluant.

Melting point: 78–81° C.

EXAMPLE 20

Dimethyl 2-{4-[2-(6-benzoyl-2-oxo-1,3-benzoxazol-3(2H)-yl)ethoxy]benzylidene}malonate The procedure is as in Example 1, starting from the compound obtained in Preparation 5 and with the replacement of diethyl malonate with dimethyl malonate.

Melting point: 173–176° C.

EXAMPLE 21

Dimethyl 2-{4-[2-(6-benzoyl-2-oxo-1,3-benzoxazol-3(2H)-yl)ethoxy]benzyl}malonate The procedure is as in Example 18, starting from the compound obtained in Example 20.

EXAMPLE 22

Dimethyl 2-{4-[2-(6-benzyl-2-oxo-1,3-benzoxazol-3 (2H)-yl)ethoxy]benzyl}malonate The procedure is as in Example 19, starting from the compound obtained in Example 21.

Melting point: 73–75° C.

EXAMPLE 23

3-{4-[2-(2-Oxo-1,3-benzoxazol-3(2H)-yl)ethoxy] phenyl}-2-propenoic acid

Dissolve the compound obtained in Preparation 1 (1 g) in a toluene-dioxane mixture (10 ml/20 ml). Add malonic acid (0.92 g) and α-picoline (0.87 ml). Stir the mixture magnetically in an oil bath at 70–80° C. for 72 hours. Remove the toluene-dioxane mixture by evaporation under reduced pressure. Take up the resulting oil in an aqueous 0.1N sodium carbonate solution and extract twice with 50 ml of ethyl acetate each time. Acidify the aqueous phase with a 6N hydrochloric acid solution until a pH of 1 is obtained, and suction-filter off the precipitate that has formed. Wash the latter with petroleum ether and recrystallise it from a 4/6 cyclohexane/toluene mixture.

Melting point: 199–200° C.

EXAMPLE 24

3-{4-[2-(2-Oxo-1,3-benzoxazol-3(2H)-yl)ethoxy] phenyl}-2-propanoic acid

Dissolve the compound obtained in Example 23 (0.45 g) in a methanol-dioxane mixture (10 ml/20 ml) and add palladium-on-carbon (0.14 g). Stir the mixture magnetically at ambient temperature under a hydrogen atmosphere for 16 hours. Remove the palladium-on-carbon by filtration and remove the methanol-dioxane mixture by evaporation under reduced pressure. Precipitate the residual oil in ether, remove the resulting precipitate by filtration and recrystallise it from a 5/5 cyclohexane/toluene mixture.

Melting point: 147–148° C.

EXAMPLE 25

3-{4-[2-(2-Oxo-1,3-benzothiazol-3(2H)-yl)ethoxy] phenyl}-2-propenoic acid

The procedure is as in Example 23 starting from the compound obtained in Preparation 2 but, after having acidified the aqueous phase to pH 1 using a 6N hydrochloric acid solution, extract twice with 50 ml of ethyl acetate each time. Dry the organic phase over magnesium sulphate and remove the ethyl acetate by evaporation under reduced pressure. Suction-filter off the resulting solid precipitate, wash it with ether and recrystallise it from an 8/2 cyclohexane/toluene mixture.

Melting point: 199–201° C.

EXAMPLE 26

3-{4-[2-(2-Oxo-1,3-benzothiazol-3(2H)-yl)ethoxy] phenyl}-2-propanoic acid

The procedure is as in Example 24 starting from the compound obtained in Example 25 but, after evaporating off the solvents under reduced pressure, suction-filter off the resulting solid precipitate with ether and recrystallise it from a 7/3 cyclohexane/toluene mixture.

Melting point: 168–170° C.

EXAMPLE 27

Dimethyl 2-{4-[2-(2-oxo[1,3]oxazolo[4,5-b]pyrid-3 (2H)-yl)ethoxy]benzylidene}malonate The procedure is as in Example 1, starting from the compound obtained in Preparation 6 and with the replacement of diethyl malonate with dimethyl malonate.

EXAMPLE 28

Dimethyl 2-{4-[2-(2-oxo[1,3]oxazolo[4,5-b]pyrid-3 (2H)-yl)ethoxy]benzyl}malonate The procedure is as in Example 18, starting from the compound obtained in Example 27.

Oil.

EXAMPLE 29

Dimethyl 2-{4-[2-(1H-pyrrolo[2,3-b]pyrid-1-yl) ethoxy]benzylidene}malonate

The procedure is as in Example 1, starting from the compound obtained in Preparation 7 and with the replacement of diethyl malonate with dimethyl malonate.

EXAMPLE 30

Dimethyl 2-{4-[2-(1H-pyrrolo[2,3-b]pyrid-1-yl) ethoxy]benzyl}malonate

The procedure is as in Example 18, starting from the compound obtained in Example 29.

Oil.

EXAMPLE 31

Methyl 3-{4-[2-(6-benzoyl-2-oxo-1,3-benzothiazol-3(2H)-yl)ethoxy]phenyl}-2-propenoate Under a nitrogen atmosphere, 1.8 equivalents of sodium hydride are dissolved in THF. 1.4 equivalents of methyl phosphonoacetate are then added dropwise at 0° C. The reaction mixture is stirred for from 15 to 20 minutes and then 1 equivalent of the compound obtained in Preparation 4 are added. After 24 hours, the mixture is hydrolysed with 100 ml of water and filtered, and the resulting precipitate is recrystallised from methanol to yield the title product.

Melting point: 144–146° C.

EXAMPLE 32

Methyl 3-{4-[2-(6-benzoyl-2-oxo-1,3-benzothiazol-3(2H)-yl)ethoxy]-phenyl}propanoate The compound obtained in Example 31 is dissolved in a methanol/dioxane mixture and then a catalytic amount of palladium-on-carbon is added. The reaction is stirred at ambient temperature under a hydrogen atmosphere for from 6 to 15 hours. The carbon is then filtered off and the solvents are removed by evaporation in vacuo. The resulting residue is recrystallised from methanol to yield the title product.

Melting point: 74–77° C.

EXAMPLE 33

Dimethyl 2-{4-[2-(6-[hydroxy(phenyl)methyl]-2-oxo-1,3-benzoxazol-3(2H)-yl)ethoxy] benzyl}malonate The compound obtained in Example 21 is dissolved in methanol and 0.25 equivalents of sodium borohydride are added. The reaction mixture is stirred at ambient temperature for 24 hours, then the methanol is evaporated off in vacuo and the resulting residue is purified by flash chromatography using an ethyl acetate/cyclohexane mixture as eluant. The title compound obtained in that way is recrystallised from isopropyl ether.

Melting point: 84–87° C.

EXAMPLE 34

Methyl 3-{4-[2-(6-benzoyl-2-oxo-1,3-benzoxazol-3(2H)-yl)ethoxy]phenyl}-2-propenoate The procedure is as in Example 31, with the replacement of the compound obtained in Preparation 4 with the compound obtained in Preparation 5.

Melting point: 170–173° C.

EXAMPLE 35

Methyl 3-{4-[2-(6-benzoyl-2-oxo-1,3-benzoxazol-3(2H)-yl)ethoxy]phenyl}propanoate The procedure is as in Example 32, starting from the compound obtained in Example 34.

Melting point: 100–103° C.

EXAMPLE 36

Dimethyl 2-{4-[2-(6-[hydroxy(phenyl)methyl]-2-oxo-1,3-benzothiazol-3(2H)-yl)ethoxy] benzyl}malonate The procedure is as in Example 33, starting from the compound obtained in Example 18.

Melting point: 153–156° C.

EXAMPLE 37

Dimethyl 2-{4-[2-(6-(2-chlorobenzoyl)-2-oxo-1,3-benzothiazol-3(2H)-yl)ethoxy]benzylidene}malonate Step A: 6-(2-Chlorobenzoyl)-1,3-benzothiazol-2(3H)-one The procedure is as in Step A of Preparation 4, with the replacement of benzoic acid with 2-chlorobenzoic acid.

Step B: Dimethyl 2-{4-[2-(6-(2-chlorobenzoyl)-2-oxo-1,3-benzothiazol-3(2H)-yl)ethoxy]benzylidene}malonate The compound obtained in Step A is dissolved in DMF and 2 equivalents of potassium carbonate are added. After stirring for 20 minutes at 80° C., 1.2 equivalents of dimethyl 2-[4-(2-chloroethoxy)benzylidene]malonate are added and the reaction is heated for 12 hours. The reaction mixture is then hydrolysed in water and filtered, and the resulting precipitate is recrystallised from methanol to yield the title product.

Melting point: 145–149° C.

EXAMPLE 38

Dimethyl 2-{4-[2-(6-[(methoxyimino)(phenyl) methyl]-2-oxo-1,3-benzothiazol-3(2H)-yl)ethoxy] benzyl}malonate The compound obtained in Example 18 is dissolved in a minimum of methanol and then 4 equivalents of O-methylhydroxylamine, previously dissolved in a few milliliters of water, and 4.5 equivalents of pyridine are added in succession. The reaction mixture is heated at reflux for 24 hours and then hydrolysed in water and filtered; the resulting precipitate is recrystallised from methanol.

Melting point: 68–72° C.

EXAMPLE 39

Dimethyl 2-{4-[2-(2-oxo-6-(3-pyridylcarbonyl)-1,3-benzothiazol-3(2H)-yl)ethoxy]benzylidene}malonate The procedure is as in Example 37, with the replacement of 2-chlorobenzoic acid with nicotinic acid in Step A.

The recrystallisation solvent is absolute ethanol.
Melting point: 130–134° C.

EXAMPLE 40

Dimethyl 2-{4-[2-(6-(2-chlorobenzoyl)-2-oxo-1,3-benzothiazol-3(2H)-yl)ethoxy]benzyl}malonate The compound obtained in Example 37 is dissolved in a methanol/THF/dioxane solvent mixture and then a catalytic amount of palladium-on-carbon is added and the reaction is stirred at ambient temperature under a hydrogen atmosphere. The palladium-on-carbon is then filtered off and the solvents are removed by evaporation under reduced pressure. The resulting residue is taken up in isopropyl ether and stirred magnetically. The resulting precipitate is filtered off and recrystallised from methanol.
Melting point: 104–108° C.

EXAMPLE 41

Dimethyl 2-{4-[2-(6-(3-chlorobenzoyl)-2-oxo-1,3-benzothiazol-3(2H)-yl)ethoxy]benzylidene}malonate The procedure is as in Example 37, with the replacement of 2-chlorobenzoic acid with 3-chlorobenzoic acid in Step A.
Melting point: 234–238° C.

EXAMPLE 42

Dimethyl 2-{4-[2-(6-([1,1'-biphenyl]-4-ylcarbonyl)-2-oxo-1,3-benthiazol-3(2H)-yl)ethoxy]benzylidene}malonate The procedure is as in Example 37, with the replacement of 2-chlorobenzoic acid with [1,1'-biphenyl]-4-carboxylic acid in Step A.
Melting point: 168° C.

EXAMPLE 43

Dimethyl 2-{4-[2-(6-(4-chlorobenzoyl)-2-oxo-1,3-benzothiazol-3(2H)-yl)ethoxy]benzylidene}malonate The procedure is as in Example 37, with the replacement of 2-chlorobenzoic acid with 4-chlorobenzoic acid in Step A.
Melting point: 234–238° C.

EXAMPLE 44

Dimethyl 2-{4-[2-(6-[(hydroxyimino)(phenyl)methyl]-2-oxo-1,3-benzothiazol-3(2H)-yl)ethoxy]benzyl}malonate The procedure is as in Example 38, with the replacement of O-methylhydroxylamine with hydroxylamine hydrochloride.
Melting point: 161–162° C.

EXAMPLE 45

Dimethyl 2-{4-[2-(6-([1,1'-biphenyl]-4-ylcarbonyl)-2-oxo-1,3-benzothiazol-3(2H)-yl)ethoxy]benzyl}malonate The procedure is as in Example 40, starting from the compound obtained in Example 42.
Melting point: 95–96° C.

EXAMPLE 46

Dimethyl 2-{4-[2-(6-butyryl-2-oxo-1,3-benzothiazol-3(2H)-yl)ethoxy]benzylidene}malonate The procedure is as in Example 37, with the replacement of 2-chlorobenzoic acid with butyric acid in Step A.
The recrystallisation solvent is an ethyl acetate/cyclohexane mixture.
Melting point: 154–155° C.

EXAMPLE 47

Dimethyl 2-{4-[2-(6-(1-naphthoyl)-2-oxo-1,3-benzothiazol-3(2H)-yl)ethoxy]benzylidene}malonate The procedure is as in Example 37, with the replacement of 2-chlorobenzoic acid with naphthoic acid in Step A.
Melting point: 143–144° C.

EXAMPLE 48

Dimethyl 2-{4-[2-(6-([1,1'-biphenyl]-4-ylmethyl)-2-oxo-1,3-benzothiazol-3(2H)-yl)ethoxy]benzyl}malonate The compound obtained in Example 45 is dissolved in 15 to 20 equivalents of trifluoroacetic acid and 2.5 equivalents of triethylsilane are added. The reaction mixture is stirred at ambient temperature for from 24 to 72 hours, and is then hydrolysed with water and extracted with ether. The organic phases are collected, dried over magnesium sulphate and evaporated in vacuo, and the resulting residue is recrystallised from ethyl acetate to yield the title product.
Melting point: 122° C.

EXAMPLE 49

Dimethyl 2-{4-[2-(6-(1-naphthoyl)-2-oxo-1,3-benzothiazol-3(2H)-yl)ethoxy]benzyl}malonate The procedure is as in Example 40, starting from the compound obtained in Example 47. The recrystallisation solvent is isopropyl ether.
Melting point: 62–63° C.

EXAMPLE 50

Dimethyl 2-{4-[2-(6-(3-chlorobenzoyl)-2-oxo-1,3-benzothiazol-3(2H)-yl)ethoxy]benzyl}malonate The procedure is as in Example 40, starting from the compound obtained in Example 41. The recrystallisation solvent is isopropyl ether.
Melting point: 90–94° C.

EXAMPLE 51

Dimethyl 2-{4-[2-(6-(2-chlorobenzyl)-2-oxo-1,3-benzothiazol-3(2H)-yl)ethoxy]benzyl}malonate The procedure is as in Example 48, starting from the compound obtained in Example 40. The recrystallisation solvent is petroleum ether.
Melting point: 92–96° C.

EXAMPLE 52

Dimethyl 2-{4-[2-(6-(3-chlorobenzyl)-2-oxo-1,3-benzothiazol-3(2H)-yl)ethoxy]benzyl}malonate The procedure is as in Example 48, starting from the compound obtained in Example 50. The recrystallisation solvent is petroleum ether.

EXAMPLE 53

Dimethyl 2-{4-[2-(6-butyryl-2-oxo-1,3-benzothiazol-3(2H)-yl)ethoxy]benzyl}malonate The procedure is as in Example 40, starting from the compound obtained in Example 46. Purification is carried out on silica.

Melting point: 74–75° C.

EXAMPLE 54

Dimethyl 2-{4-[2-(6-(1-naphthylmethyl)-2-oxo-1,3-benzothiazol-3(2H)-yl)ethoxy]benzyl}malonate The procedure is as in Example 48, starting from the compound obtained in Example 49. The recrystallisation solvent is toluene.

Melting point: 120–122° C. cl EXAMPLE 55

Dimethyl 2-{4-[2-(6-butyl-2-oxo-1,3-benzothiazol-3(2H)-yl)ethoxy]benzyl}malonate The procedure is as in Example 48, starting from the compound obtained in Example 53. The recrystallisation solvent is hexane.

Melting point: 73–74° C.

EXAMPLE 56

Dimethyl 2-{4-[2-(2-oxo-6-(3-pyridylcarbonyl)-1,3-benzothiazol-3(2H)-yl)ethoxy]benzyl}malonate The procedure is as in Example 40, starting from the compound obtained in Example 39. Purification is carried out on silica.

Melting point: 129–134° C.

EXAMPLE 57

Dimethyl 2-{4-[2-(6-(4-chlorobenzoyl)-2-oxo-1,3-benzothiazol-3(2H)-yl)ethoxy]benzyl}malonate The procedure is as in Example 40, starting from the compound obtained in Example 43. Purification is carried out on silica.

Melting point: 80–85° C.

EXAMPLE 58

2-{4-[2-(6-Benzoyl-2-oxo-1,3-benzothiazol-3(2H)-yl)ethoxy]benzyl}malonic acid

The procedure is as in Example 11, starting from-the compound obtained in Example 18.

EXAMPLE 59

Dimethyl 2-{4-[2-(6-(4-methoxybenzoyl)-2-oxo-1,3-benzothiazol-3(2H)-yl)ethoxy]benzylidene}malonate The procedure is as in Example 37, with the replacement of 2-chlorobenzoic acid with 4-methoxybenzoic acid in Step A.

The recrystallisation solvent is ethyl acetate.

Melting point: 144–145° C.

EXAMPLE 60

Dimethyl 2-{4-[2-(6-(2-naphthoyl)-2-oxo-1,3-benzothiazol-3(2H)-yl)ethoxy]benzyl}malonate The procedure is as in Example 40, starting from the compound obtained in Example 70. The recrystallisation solvent is hexane.

Melting point: 87° C.

EXAMPLE 61

Dimethyl 2-{4-[2-(6-(4-methoxybenzoyl)-2-oxo-1,3-benzothiazol-3(2H)-yl)ethoxy]benzyl}malonate The procedure is as in Example 40, starting from the compound obtained in Example 59.

Melting point: 114–117° C.

EXAMPLE 62

Dimethyl 2-{4-[2-(6-(4-chlorobenzyl)-2-oxo-1,3-benzothiazol-3(2H)-yl)ethoxy]benzyl}malonate The procedure is as in Example 48, starting from the compound obtained in Example 57. Purification is carried out on silica.

Melting point: 40–45° C.

EXAMPLE 63

2-{4-[2-(6-Benzoyl-2-oxo-1,3-benzothiazol-3(2H)-yl)ethoxy]benzyl}-3-methoxy-3-oxopropanoic acid The procedure is as in Example 9, starting from the compound obtained in Example 18.

EXAMPLE 64

Dimethyl 2-{4-[2-(6-[(2-chlorophenyl)(methoxyimino)methyl]-2-oxo-1,3-benzothiazol-3(2H)-yl)ethoxy]benzylidene}malonate The procedure is as in Example 68, starting from the compound obtained in Example 37. The recrystallisation solvent is methanol.

Melting point: decomposition at 142–146° C.

EXAMPLE 65

Dimethyl 2-{4-[2-(6-[(3-chlorophenyl)(methoxyimino)methyl]-2-oxo-1,3-benzothiazol-3(2H)-yl)ethoxy]benzyl}malonate The procedure is as in Example 38, starting from the compound obtained in Example 50.

Melting point: decomposition at 121–125° C.

EXAMPLE 66

Dimethyl 2-{4-[2-(6-(4-methoxybenzyl)-2-oxo-1,3-benzothiazol-3(2H)-yl)ethoxy]benzyl}malonate The procedure is as in Example 48, starting from the compound obtained in Example 61. The recrystallisation solvent is methanol.

Melting point: 112–113° C.

EXAMPLE 67

Dimethyl 2-{4-[2-(6-(2-naphthylmethyl)-2-oxo-1,3-benzothiazol-3(2H)-yl)ethoxy]benzyl}malonate The procedure is as in Example 48, starting from the compound obtained in Example 60. The recrystallisation solvent is methanol.

Melting point: 104–105° C.

EXAMPLE 68

Dimethyl 2-{4-[2-(6-[(3-chlorophenyl)(methoxyimino)methyl]-2-oxo-1,3-benzothiazol-3(2H)-yl)ethoxy]benzylidene}malonate The compound obtained in Example 41 is dissolved in a minimum of methanol, and then 4 equivalents of O-methylhydroxylamine, previously dissolved in a few milliliters of water, and 4.5 equivalents of pyridine are added in succession. The reaction mixture is heated at reflux for 24 hours and then hydrolysed in water and filtered; the resulting precipitate is recrystallised from acetonitrile.

Melting point: decomposition at 78–82° C. then >200° C.

EXAMPLE 69

Dimethyl 2-{4-[2-(6-[(4-chlorophenyl)(methoxyimino)methyl]-2-oxo-1,3-benzothiazol-3(2H)-yl)ethoxy]benzylidene}malonate The procedure is as in Example 68, starting from the compound obtained in Example 43.

Melting point: decomposition at 118–121° C. then 158–162° C.

EXAMPLE 70

Dimethyl 2-{4-[2-(6-(2-naphthoyl)-2-oxo-1,3-benzothiazol-3(2H)-yl)ethoxy]benzylidene}malonate The procedure is as in Example 37, with the replacement of 2-chlorobenzoic acid with 2-naphthoic acid in Step A.

The recrystallisation solvent is ethyl acetate.

Melting point: 164° C.

EXAMPLE 71

Dimethyl 2-{4-[2-(6-[[1,1'-biphenyl]-4-yl(methoxyimino)methyl]-2-oxo-1,3-benzothiazol-3(2H)-yl)ethoxy]benzyl}malonate The procedure is as in Example 38, starting from the compound obtained in Example 45.

Melting point 63–64° C.

EXAMPLE 72

Dimethyl 2-{4-[2-(6-[[1,1'-biphenyl]-4-yl(methoxyimino)methyl]-2-oxo-1,3-benzothiazol-3(2H)-yl)ethoxy]benzylidene}malonate The procedure is as in Example 68, starting from the compound obtained in Example 42. The recrystallisation solvent is methanol.

Melting point: decomposition at 131–132° C.

EXAMPLE 73

Dimethyl 2-{4-[2-(6-[(2-chlorophenyl)(methoxyimino)methyl]-2-oxo-1,3-benzothiazol-3(2H)-yl)ethoxy]benzyl}malonate The procedure is as in Example 38, starting from the compound obtained in Example 40.

Melting point: decomposition at 92–95° C.

EXAMPLE 74

3-Methoxy-3-oxo-2-{4-[2-(1H-pyrrolo[2,3-b]pyrid-1-yl)ethoxy]benzyl}propanoic acid The compound obtained in Example 30 is dissolved in 5 ml of methanol and 3 ml of THF. The mixture is cooled to 0° C. and 0.44 ml of a 2M sodium hydroxide solution is added dropwise. After stirring for 1 hour 30 minutes at ambient temperature, the solvents are removed by evaporation under reduced pressure and the resulting residue is taken up in water and extracted with ethyl acetate. The aqueous phase is acidified with a 2M hydrochloric acid solution and extracted with ethyl acetate. The organic phase is dried over magnesium sulphate, filtered, and evaporated under reduced pressure. The resulting residue is taken up in a minimum of ethyl acetate and precipitated with pentane to yield the title product after filtration.

Melting point: 120–122° C.

EXAMPLE 75

Dimethyl 2-{4-[2-(6-(benzoylamino)-2-oxo-1,3-benzothiazol-3(2H)-yl)ethoxy]benzyl}malonate The procedure is as in Example 40, starting from the compound obtained in Example 76.

Melting point: 90–94° C.

EXAMPLE 76

Dimethyl 2-{4-[2-(6-(benzoylamino)-2-oxo-1,3-benzothiazol-3(2H)-yl)ethoxy]benzylidene}malonate The procedure is as in Example 37.

Melting point: 186–190° C.

EXAMPLE 77

3-{4-[2-(6-Benzyl-2-oxo-1,3-benzothiazol-3(2H)-yl)ethoxy]phenyl}propanoic acid

The compound obtained in Example 78 is dissolved in a methanol/THF mixture and 1.2 equivalents of sodium hydroxide are added dropwise. The reaction mixture is stirred at ambient temperature for 24 hours and then evaporated, the resulting residue is taken up in water and extracted twice with ether, and the aqueous phase is acidified with a 6N hydrochloric acid solution. The resulting precipitate is filtered off and recrystallised from methanol to yield the title product.

Melting point: 158–163° C.

EXAMPLE 78

Methyl 3-{4-[2-(6-benzyl-2-oxo-1,3-benzothiazol-3(2H)-yl)ethoxy]phenyl}propanoate The procedure is as in Example 48, starting from the compound obtained in Example 32. The recrystallisation solvent is methanol.

Melting point: 71–75° C.

EXAMPLE 79

Methyl 3-{4-[2-(6-[(methoxyimino)(phenyl)methyl]-2-oxo-1,3-benzothiazol-3(2H)-yl)ethoxy]phenyl}propanoate The procedure is as in Example 38, starting from the compound obtained in Example 32.

EXAMPLE 80

3-{4-[2-(6-Benzoyl-2-oxo-1,3-benzothiazol-3(2H)-yl)ethoxy]phenyl}propanoic acid

The procedure is as in Example 77, starting from the compound obtained in Example 32. The recrystallisation solvent is a toluene/cyclohexane mixture.

Melting point: 169–173° C.

EXAMPLE 81

2-{4-[2-(1H-Pyrrolo[2,3-b]pyrid-1-yl)ethoxy]benzyl}malonic acid

The compound obtained in Example 30 (274 mg) is dissolved in 5 ml of methanol, 2.5 ml of THF and 5 ml of water. A 2M solution of sodium hydroxide is added (1.8 ml) and the reaction mixture is stirred for 4 days at ambient temperature. The solvents are then evaporated off under reduced pressure, and the resulting residue is taken up in water and extracted with ethyl acetate. The aqueous phase is cooled to 0° C. and acidified with a 2M hydrochloric acid solution, and the resulting solid is filtered off.

Melting point: 182–184° C.

EXAMPLE 82

Methyl 2-{4-[2-(6-benzoyl-2-oxo-1,3-benzothiazol-3(2H)-yl)ethoxy]benzyl}-3-(methylamino)-3-oxopropanoate The compound obtained in Example 63 is dissolved in anhydrous dichloromethane and then 1.5 equivalents of thionyl chloride are added and the mixture is heated at reflux for 1 hour 30 minutes. The reaction mixture is then cooled using an ice bath, and 1.2 equivalents of methylamine are added via the top of the condenser. The reaction mixture is stirred for one hour and is then extracted with dichloromethane. The organic phases are washed with a sodium carbonate solution, and with water, and are then filtered, dried over magnesium sulphate and evaporated under reduced pressure. The resulting residue is purified by flash chromatography using an ethyl acetate/cyclohexane mixture as eluant. The resulting title product is recrystallised from a toluene/cyclohexane mixture.

Melting point: 162–164° C.

EXAMPLE 83

Dimethyl 2-{4-[2-(6-(anilinocarbonyl)-2-oxo-1,3-benzothiazol-3(2H)-yl)ethoxy]benzyl}malonate The procedure is as in Example 40, starting from the compound obtained in Example 84.

Melting point: 104–109° C.

EXAMPLE 84

Dimethyl 2-{4-[2-(6-(anilinocarbonyl)-2-oxo-1,3-benzothiazol-3(2H)-yl)ethoxy]benzylidene}malonate The procedure is as in Example 37.

Melting point: 102–105° C.

EXAMPLE 85

Dimethyl 2-{4-[2-(2-oxo-6-[2-phenylethenyl]-1,3-benzothiazol-3(2H)-yl)ethoxy]benzylidene}malonate Step A: 6-Nitro-1,3-benzothiazol-2(3H)-one 0.1 mol of benzothiazolinone is dissolved in 100 ml of acetic anhydride and the solution is cooled to −10° C. 10 ml of nitric acid are then added dropwise, and the reaction is stirred for 2 hours. The resulting precipitate is filtered off and washed with water, and then purified by chromatography (eluant CH$_2$Cl$_2$ then AcOEt) to yield the title product, which is recrystallised from ethanol.

Melting point: 248–253° C.

Step B: 6-Amino-1,3-benzothiazol-2(3H)-one

The compound obtained in Step A (0.036 mol) is dissolved in 90 ml of methanol, and then 2.5 g of palladium-on-carbon and 18 g of ammonium formate are added in succession and the mixture is heated at reflux for 18 hours. 40 ml of dioxane are added and refluxing is continued for 24 hours. The palladium-on-carbon is then filtered off. The reaction mixture is concentrated, the resulting precipitate is filtered off, and the filtrate is evaporated under reduced pressure. The resulting residue is taken up in a 1N hydrochloric acid solution and extracted twice with 50 ml of ethyl acetate each time. The aqueous phase is rendered alkaline with a 10% potassium carbonate solution and extracted twice with 50 ml of ethyl acetate each time. The organic phase is dried and then evaporated under reduced pressure, and the resulting precipitate is recrystallised from acetonitrile.

Melting point: 220–224° C.

Step C: 6-(2-Phenylethenyl)-1,3-benzothiazol-2(3H)-one

The compound obtained in Step B (1 g) is dissolved in HBF$_4$ (10 ml) and the mixture is cooled to 0° C. 0.44 g of NaNO$_2$ previously dissolved in water is then added and the reaction is stirred at 0° C. for 1 hour. The resulting precipitate is filtered off and washed with ether, ground with BF$_3$ (4.5 mmol) and palladium acetate (0.2 mmol), and then placed under a nitrogen atmosphere before the addition of 15.1 ml of anhydrous dioxane. The reaction mixture is stirred for 5 hours at ambient temperature and then hydrolysis is carried out with 50 ml of water and extraction is carried out twice with 30 ml ether each time. The organic phase is dried over MgSO$_4$ and then evaporated under reduced pressure. The resulting precipitate is washed with isopropyl ether and recrystallised from methanol.

Melting point:179° C.

Step D: Dimethyl 2-{4-[2-(2-oxo-6-[2-phenylethenyl]-1,3-benzothiazol-3(2H)-yl)-ethoxy]benzylidene}malonate The procedure is as in Step B of Example 37, starting from the compound obtained in Step C.

Melting point: 90° C.

EXAMPLE 86

Dimethyl 2-(4-{[2-(2-oxo-1,3-benzothiazol-3(2H)-yl)ethyl]amino}benzylidene)malonate The procedure is as in Step B of Example 37, starting from thiazolinone and with the replacement of dimethyl 2-{4-[2-chloroethoxy]benzylidene}malonate with dimethyl 2-{4-[(2-chloroethyl)amino]benzylidene}malonate.

EXAMPLE 87

Dimethyl 2-(4-{[2-(6-benzoyl-2-oxo-1,3-benzothiazol-3(2H)-yl)ethyl]amino}benzylidene)malonate The procedure is as in Step B of Example 37, starting from the compound obtained in Step A of Preparation 4 and with the replacement of dimethyl 2-{4-[2-chloroethoxy]benzylidene}malonate with dimethyl 2-{4-[(2-chloroethyl)amino]benzylidene}malonate.

EXAMPLE 88

Dimethyl 2-(4-{[2-(6-benzoyl-2-oxo-1,3-benzothiazol-3(2H)-yl)ethyl]amino}benzyl)malonate The procedure is as in Example 40, starting from the compound obtained in Example 87.

EXAMPLE 89

Dimethyl 2-{4-[2-(2-oxo-6-[2-phenylethenyl]-1,3-benzothiazol-3(2H)-yl)ethoxy]benzyl}malonate The procedure is as in Step B of Example 37 starting from the compound obtained in Example 85, with the replacement of dimethyl 2-[4-(2-chloroethoxy)benzylidene]malonate with dimethyl 2-[4-(2-chloroethoxy)benzyl]malonate.

Melting point: 103–107° C.

EXAMPLE 90

Dimethyl 2-{4-[2-(6-(3-methylbenzoyl)-2-oxo-1,3-benzothiazol-3(2H)-yl)ethoxy]benzylidene}malonate The procedure is as in Example 37, with the replacement of 2-chlorobenzoic acid with 3-methylbenzoic acid in Step A.

Melting point: 153–154° C.

EXAMPLE 91

Ethyl 2-benzoyl-3-{4-[2-(6-benzoyl-2-oxo-1,3-benzothiazol-3(2H)-yl-ethoxy]phenyl}-2-propenoate A mixture consisting of 5 g of the compound obtained in Preparation 4, 2.14 ml of ethyl benzoylacetate, 0.05 equivalents of pyridine, and 0.15 ml of glacial acetic acid in 200 ml of anhydrous toluene, is heated at reflux for 40 hours, the water formed being removed by azeotropic distillation using a Dean-Stark apparatus. The reaction mixture is then filtered and the filtrate is evaporated under reduced pressure. The title product is purified by chromatography (eluant AcOEt/cyclohexane: 3/7), taken up in diisopropyl ether and recrystallised from toluene.

Melting point: 189–190° C.

EXAMPLE 92

Ethyl 2-{4-[2-(6-benzoyl-2-oxo-1,3-benzothiazol-3(2H)-yl)ethoxy]benzyl}-3-oxo-3-phenylpropanoate The compound obtained in Example 91 is dissolved in 45 ml of a EtOH95/dioxane/THF mixture (1/4/4) and then placed in vacuo under a hydrogen atmosphere. The reaction mixture is stirred for 4 hours 30 minutes and then filtered, and the filtrate is evaporated under reduced pressure. The title product is purified by chromatography (eluant AcOEt/cyclohexane: 3/7), taken up in diisopropyl ether and recrystallised from toluene/cyclohexane.

Melting point: 93–95° C.

EXAMPLE 93

Dimethyl 2-{4-[2-(1H-pyrrolo[3,2-c]pyrid-1-yl)ethoxy]benzylidene}malonate

The procedure is as in Example 1, starting from the compound obtained in Preparation 8 and with the replacement of diethyl malonate with dimethyl malonate.

EXAMPLE 94

Dimethyl 2-{4-[2-(1H-pyrrolo[3,2-c]pyrid-1-yl)ethoxy]benzyl}malonate

The procedure is as in Example 18, starting from the compound obtained in Example 93.

EXAMPLE 95

3-Methoxy-3-oxo-2-{4-[2-(1H-pyrrolo[3,2-c]pyrid-1-yl)ethoxy]benzylpropanoic acid The procedure is as in Example 74, starting from the compound obtained in Example 94.

EXAMPLE 96

2-{4-[2-(1H-Pyrrolo[3,2-c]pyrid-1-yl)ethoxy]benzyl}malonic acid

The procedure is as in Example 81, starting from the compound obtained in Example 94.

EXAMPLE 97

Methyl 2-{4-[2-(6-benzyl-2-oxo-1,3-benzothiazol-3(2H)-yl)ethoxy]benzyl}-3-[2-(methylamino)phenyl]-3-oxopropanoate The procedure is as in Example 37, with the replacement of 2-chlorobenzoic acid with benzoic acid in Step A and with the replacement of dimethyl 2-[4-(2-chloroethoxy)benzylidene]malonate with methyl 2-[4-(2-chloroethoxy)benzyl]-3-[2-(methylamino)phenyl]-3-oxopropanoate in Step B.

EXAMPLE 98

Methyl 3-{4-[2-(1H-pyrrolo[2,3-b]pyrid-1-yl)ethoxy]phenyl}-2-propenoate

The procedure is as in Example 31, with replacement of the product obtained in Preparation 4 with the product obtained in Preparation 7.

EXAMPLE 99

Methyl 3-{4-[2-(1H-pyrrolo[2,3-b]pyrid-1-yl)ethoxy]phenyl}propanoate

The procedure is as in Example 32, starting from the compound obtained in Example 98.

Pharmacological Study

Example A

Acute Toxicity Study

The acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

Example B

Effectiveness in Genetic Models

Mutations in laboratory animals and also different sensitivities to dietary regimens have allowed the development of animal models having non-insulin dependent diabetes and hyperlipidaemia associated with obesity and with resistance to insulin.

Genetic mice models (ob/ob) (Diabetes, 1982, 31 (1), 1–6) and Zucker (fa/fa) rats have been developed by various laboratories in order to understand the physiopathology of those diseases and test the effectiveness of new antidiabetic compounds (Diabetes, 1983, 32, 830–838).

Antidiabetic and Hypolipidaemic Effect in the ob/ob Mouse

The 10-week-old female ob/ob mouse (Harlan) is used for the in vivo tests. The animals are kept in a light-darkness cycle of 12 hours at 25° C. The mouse has a basal hyperglycaemia of 2 g/l. The animals are randomly selected in terms of their glycaemia to form groups of six. The compounds tested by the intraperitoneal route are dissolved in a mixture of dimethyl sulphoxide (10%) and solutol (15%) to be administered at 10 mg/kg in a volume of 2.5 ml/kg twice per day for four days. By the per os route, the compounds are tested at 30 mg/kg administered in a volume of 2.5 ml/kg of 1%, HEC twice per day for four days. The control groups receive the solvents under the same conditions as the treated groups. The activity of the products is evaluated by measuring glycaemia 24 hours after the final administration and by measuring body weight daily.

The compounds of the invention demonstrate a very good capacity to lower glycaemia that is comparable to the effects obtained with rosiglitazone, which is used as reference substance, but with an insignificant variation in body weight, whereas under the same conditions rosiglitazone exhibits a significant increase of +4% in four days. Furthermore, no side effects were observed during the in vivo tests.

By way of example, the compound of Example 18, substantially reduces glycaemia by 43% when administered at 30 mg/kg per os, and by 45% when administered i.p. at 10 mg/kg.

Example C

Pharmaceutical Composition

| | |
|---|---|
| 1000 tablets each containing a dose of 5 mg of dimethyl 2-{4-[2-(6-benzoyl-2-oxo-1,3-benzothiazol-3(2H)-yl)ethoxy]benzyl}malonate (Example 18) | 5 g |
| wheat starch | 20 g |
| maize starch | 20 g |
| lactose | 30 g |
| magnesium stearate | 2 g |
| silica | 1 g |
| hydroxypropyl cellulose | 2 g |

What is claimed is:
1. A compound of formula (I):

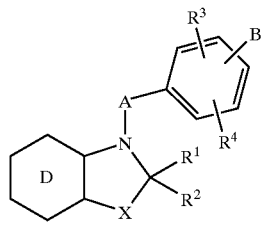

wherein:
X represents oxygen or sulphur,
$R^1$ and $R^2$ together form oxo,
A represents $CH_2CH_2O$,
B represents linear or branched ($C_1$–$C_6$)alkyl or linear or branched ($C_2$–$C_6$)alkenyl, those groups being substituted by $R^5$, by a group of formula (II):

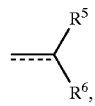

or by a group of formula (III)

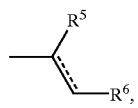

in which groups:
the representation ═══ denotes that the bond is single or double,
$R^5$ represents

wherein Z represents sulphur or oxygen and Z' represents OR or NRR',
and $R^6$ represents

wherein Z" represents Z' or R,
(wherein R and R', which may be identical or different, each represents R" or —C(Me)$_2$COOR" wherein R" represents hydrogen or linear or branched ($C_1$–$C_6$) alkyl, linear or branched ($C_2$–$C_6$)alkenyl, linear or branched ($C_2$–$C_6$)alkynyl, aryl, aryl-($C_1$–$C_6$)alkyl in which the alkyl moiety may be linear or branched, aryl-($C_2$–$C_6$)alkenyl in which the alkenyl moiety may be linear or branched, aryl-($C_2$–$C_6$)alkynyl in which the alkynyl moiety may be linear or branched, heteroaryl, heteroaryl-($C_1$–$C_6$)alkyl in which the alkyl moiety may be linear or branched, heteroaryl-($C_2$–$C_6$)alkenyl in which the alkenyl moiety may be linear or branched, heteroaryl-($C_2$–$C_6$)alkynyl in which the alkynyl moiety may be linear or branched, ($C_3$–$C_8$)cycloalkyl, ($C_3$–$C_8$)cycloalkyl-($C_1$–$C_6$)alkyl in which the alkyl moiety may be linear or branched, or linear or branched ($C_1$–$C_6$)polyhaloalkyl),
$R^3$ and $R^4$, which may be identical or different, each represents hydrogen, halogen or R, OR, or NRR' (wherein R and R' are as defined hereinbefore),
or $R^3$ and $R^4$ together with the carbon atoms carrying them, when they are carried by two adjacent carbon atoms, form a ring that has 5 or 6 ring members and that may contain a hetero atom selected from oxygen, sulphur and nitrogen,
D represents benzene substituted by

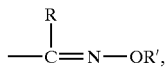

wherein R and R' are as defined hereinbefore,
wherein:
when A and B are in the ortho position in relation to one another on the benzene nucleus carrying them, B cannot represent linear or branched ($C_2$–$C_6$)-alkenylene substituted by

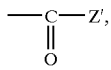

aryl is to be understood as phenyl, naphthyl, or biphenyl, which groups may be partially hydrogenated, heteroaryl is to be understood as any mono- or bi-cyclic aromatic group containing from 5 to 10 ring members, which may be partially hydrogenated on one of the rings in the case of bicyclic heteroaryls, and which contains from 1 to 3 hetero atoms selected from oxygen, nitrogen and sulphur, wherein the aryl and heteroaryl groups so defined may be substituted by from 1 to 3 groups selected from linear or branched ($C_1$–$C_6$)alkyl, linear or branched ($C_1$–$C_6$)alkoxy, carboxy, formyl, $NR_bR_c$ (wherein $R_b$ and $R_c$, which may be identical or different, each represents hydrogen, linear or branched ($C_1$–$C_6$)alkyl, aryl or heteroaryl), ester, amido, intro, cyano, O—C(Me)$_2$COOR" (wherein R" is as defined hereinbefore), and halogen, its enantiomers and diastereoisomers, and addition salts thereof with a pharmaceutically-acceptable acid or base.

2. A compound according to claim 1, wherein $R^3$ and $R^4$ simultaneously represent hydrogen.

3. A compound according to claim 1, wherein B represents alkyl or alkenyl, those groups being substituted by a group of formula (II).

4. A compound according to claim 1, wherein B represents alkyl or alkenyl, those groups being substituted by $R^5$.

5. A compound according to claim 1, which is selected from dimethyl 2-{4-[2-(6-[(methoxyimino)(phenyl)methyl]-2-oxo-1,3-benzothiazol-3(2H)-yl)ethoxy]benzyl}malonate, dimethyl 2-{4-[2-(6-[(hydroxyimino)(phenyl)methyl]-2-oxo-1,3-benzothiazol-3(2H)-yl)ethoxy]benzyl}malonate, dimethyl 2-{4-[2-(6-[(3-chlorophenyl)(methoxyimino)methyl]2-oxo-1,3-benzothiazol-3(2H)-yl)ethoxy]benzyl}malonate and dimethyl 2-{4-[2-(6-[[1,1'-biphenyl]-4-yl(methoxyimino)methyl]-2-oxo-1,3-benzothiazol-3(2H)-yl)ethoxy]benzyl}malonate, and addition salts thereof with a pharmaceutically acceptable acid or base.

6. A compound according to claim 1, which is selected from methyl 3-{4-[2-(6-[(methoxyimino)(phenyl)methyl]-2-oxo-1,3-benzothiazol-3(2H)-yl)ethoxy]phenyl}propanoate and addition salts thereof with a pharmaceutically acceptable acid or base.

7. A method for the treatment of a living body afflicted with a condition selected from hyperglycaemia and non-insulin dependent type II diabetes, comprising the step of administering to the living body an amount of a compound of claim 1 which is effective for alleviation of said condition.

8. A pharmaceutical composition useful for the treatment of a condition selected from hyperglycaemia and non-insulin dependent type II diabetes, comprising as active principle an effective amount of a compound of claim 1 together with one or more pharmaceutically-acceptable excipients or vehicles.

* * * * *

UNITED STATES PATENT AND TRADEMARK OFFICE
CERTIFICATE OF CORRECTION

PATENT NO. : 6,919,362 B2
DATED : July 9, 2005
INVENTOR(S) : Daniel Lesieur et al.

Page 1 of 1

It is certified that error appears in the above-identified patent and that said Letters Patent is hereby corrected as shown below:

Column 31,
Line 40, "A compound of formula" should be -- A compound selected from those of formula --.

Signed and Sealed this

Thirteenth Day of September, 2005

JON W. DUDAS
*Director of the United States Patent and Trademark Office*